(12) United States Patent
Rogel et al.

(10) Patent No.: US 11,948,666 B2
(45) Date of Patent: Apr. 2, 2024

(54) SYSTEMS AND PROCESSES FOR PREDICTING ASPHALTENE BLEND COMPATIBILITY

(71) Applicant: CHEVRON U.S.A. INC., San Ramon, CA (US)

(72) Inventors: Estrella Rogel, San Ramon, CA (US); Toni Miao, San Ramon, CA (US); Eddy Lee, San Ramon, CA (US); Kyle Hench, San Ramon, CA (US)

(73) Assignee: CHEVRON U.S.A. INC.

( * ) Notice: Subject to any disclaimer, the term of this patent is extended or adjusted under 35 U.S.C. 154(b) by 0 days.

(21) Appl. No.: 17/882,284

(22) Filed: Aug. 5, 2022

(65) Prior Publication Data

US 2024/0047017 A1 Feb. 8, 2024

(51) Int. Cl.
| | |
|---|---|
| *G01N 31/16* | (2006.01) |
| *G01N 21/3577* | (2014.01) |
| *G01N 21/359* | (2014.01) |
| *G01N 33/28* | (2006.01) |
| *G16C 20/30* | (2019.01) |

(52) U.S. Cl.
CPC ......... *G16C 20/30* (2019.02); *G01N 21/3577* (2013.01); *G01N 21/359* (2013.01); *G01N 31/16* (2013.01); *G01N 33/2823* (2013.01)

(58) Field of Classification Search
CPC .. G16C 20/30; G01N 21/3577; G01N 21/359; G01N 31/16; G01N 33/2823
See application file for complete search history.

(56) References Cited

U.S. PATENT DOCUMENTS

| | | |
|---|---|---|
| 9,921,203 B2 | 3/2018 | Rogel et al. |
| 2019/0169512 A1 | 6/2019 | Rogel et al. |
| 2019/0234928 A1* | 8/2019 | Kumar .............. C10G 75/00 |
| 2021/0122982 A1 | 4/2021 | Yang et al. |

OTHER PUBLICATIONS

Bambiinek et al., Compatibility of Crude Oil Blends—Processing Issues Related to Asphaltene Precipitation, Methods of Instability Prediction—A Review, Dec. 19, 2022, IN. Eng. Chemc. Res, vol. 62, pp. 2-15 (Year: 2022).*

Mahmoud et al., Compatibility Assessment of Crude Oil Blends Using Different Methods, Chemical Engineering Transaction, 2017, vol. 57, pp. 1-6. (Year: 2017).*

(Continued)

*Primary Examiner* — Christine S. Kim
(74) *Attorney, Agent, or Firm* — Hunton Andrews Kurth LLP

(57) ABSTRACT

The present disclosure advantageously refers to systems and methods for predicting an oil mixture's blend compatibility without mixing the components and/or without performing direct blend testing. The techniques described use a correlation between near infrared spectroscopic information, asphaltene solubility parameter Ra, and maltene solubility parameter Po to accurately predict blend compatibility using the equation P=Po(blend)/Ra(blend). A P≥1 indicates the blend is compatible. These techniques are useful in, for example, refineries to predict and therefore reduce or eliminate fouling due to asphaltene deposits.

19 Claims, 4 Drawing Sheets

(56) References Cited

OTHER PUBLICATIONS

Shishkova et al., Evaluation of the Different Compatibility Indices to Model and Predict Oil Colloidal Stability and its Relation to Crude Oil Desalting, Jul. 22, 2021, Resources, vol. 10, Ipp. 1-20 (Year: 2021).*

International Search Report and Written Opinion dated Oct. 19, 2023 issued in PCT/US2023/29428.

Kumar et al., "Prediction of crude oil blends compatibility and blend optimization for increasing heavy oil processing", Fuel Processing Technology 177 (2018) pp. 309-327.

Bambinek et al., "Compatibility of Crude Oil Blends—Processing Issues Related to Asphaltene Precipitation, Methods of Instability Prediction—A Review", Ind. Eng. Chem. Res. 2023, 62, 2-15, Dec. 19, 2022.

* cited by examiner

SYSTEMS AND PROCESSES FOR PREDICTING ASPHALTENE BLEND COMPATIBILITY

FIELD OF THE DISCLOSURE

The present disclosure relates to systems and methods for predicting blend compatibility of various asphaltene compositions using, for example, near infrared spectroscopy.

BACKGROUND AND SUMMARY

Fouling of heat exchangers, storage tanks, and other equipment in oil and gas processing in, for example, a refinery is often problematic. While there may be many reasons for fouling a major cause in many instances is due to a change in asphaltene amount or composition and/or a change in amount or composition of a surrounding solvent (s).

Currently, titration techniques are used as a proxy to predict fouling by determining a flocculation onset or the amount of precipitant to destabilize asphaltenes dissolved in a composition. That is, the amount of precipitant added is an indicator of the tendency towards asphaltene precipitation of the material. In this manner, if potential fouling is indicated due to precipitation, then corrective measures may be undertaken in an attempt to prevent or deter fouling.

Unfortunately, these titration techniques are often time consuming and/or require highly trained personnel. In addition, an adequate concentration of sample and other conditions needs to be established before any testing can be conducted. Yet another drawback is that the limits of detection often preclude the testing of samples containing low amounts of asphaltenes, e.g., less than 1.5%, or less than 1% asphaltenes. Accordingly, alternatives to the titration techniques are needed for refineries, as well as crude oil/product distribution and storage sites.

What is needed are more effective and cost-efficient systems for predicting fouling. It would be advantageous if such alternative techniques were relatively quick, did not require highly trained personnel, and/or could be used even with compositions having relatively low amounts of asphaltenes. Advantageously, the systems and methods described herein may meet one or more up to all of the aforementioned needs.

The present application generally pertains in one embodiment to a method of predicting a blend compatibility in a system between a first oil composition A and a second oil composition B. The method comprises obtaining a correlation between near infrared spectroscopic information, asphaltene solubility parameter Ra, and maltene solubility parameter Po for a set of samples using multivariable analysis. A near infrared spectra is obtained on the first oil composition A and the correlation is used to obtain the first oil composition A's Ra and Po. A near infrared spectra is obtained on the second oil composition B and the correlation is used to obtain the second oil composition B's Ra and Po. The Ra of the blend of the first oil composition A and the second oil composition B is determined using the equation Ra(blend)=mA RaA+mB RaB. The Po of the blend of the first oil composition A and the second oil composition B is determined using the equation Po(blend)=mA PoA+mB PoB. mA, mB are the % mass of crude oils A and B, while PoA, RaA, PoB and RaB are the parameters of the crude oils A and B that form the blend. The blend compatibility may be predicted using the equation P=Po(blend)/Ra(blend) wherein a P≥1 indicates the blend is compatible.

In another embodiment the application pertains to a system for predicting a blend compatibility between a first oil composition A and a second oil composition B. The system comprises a first oil composition A; a second oil composition B; a near infrared spectrometer configured to obtain a near infrared spectra on the first oil composition A and to obtain a near infrared spectra on the second oil composition B; and a data processor. The data processor is configured to first use a correlation between near infrared spectroscopic information, asphaltene solubility parameter Ra, and maltene solubility parameter Po for a set of samples to obtain the first oil composition A's Ra and Po and the second oil composition B's Ra and Po. The data processor determines the Ra of the blend of the first oil composition A and the second oil composition B using the equation Ra(blend)=mA RaA+mB RaB and determines the Po of the blend of the first oil composition A and the second oil composition B using the equation Po(blend)=mA PoA+mB PoB, wherein mA, mB are the % mass of crude oils A and B, while PoA, RaA, PoB and RaB are the parameters of the crude oils A and B that form the blend. The processor predicts the blend compatibility using the equation P=Po(blend)/Ra(blend) wherein a P≥1 indicates the blend is compatible.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Various embodiments of the present disclosure, together with further objects and advantages, may best be understood by reference to the following description taken in conjunction with the accompanying drawings.

DETAILED DESCRIPTION

Figure 1:
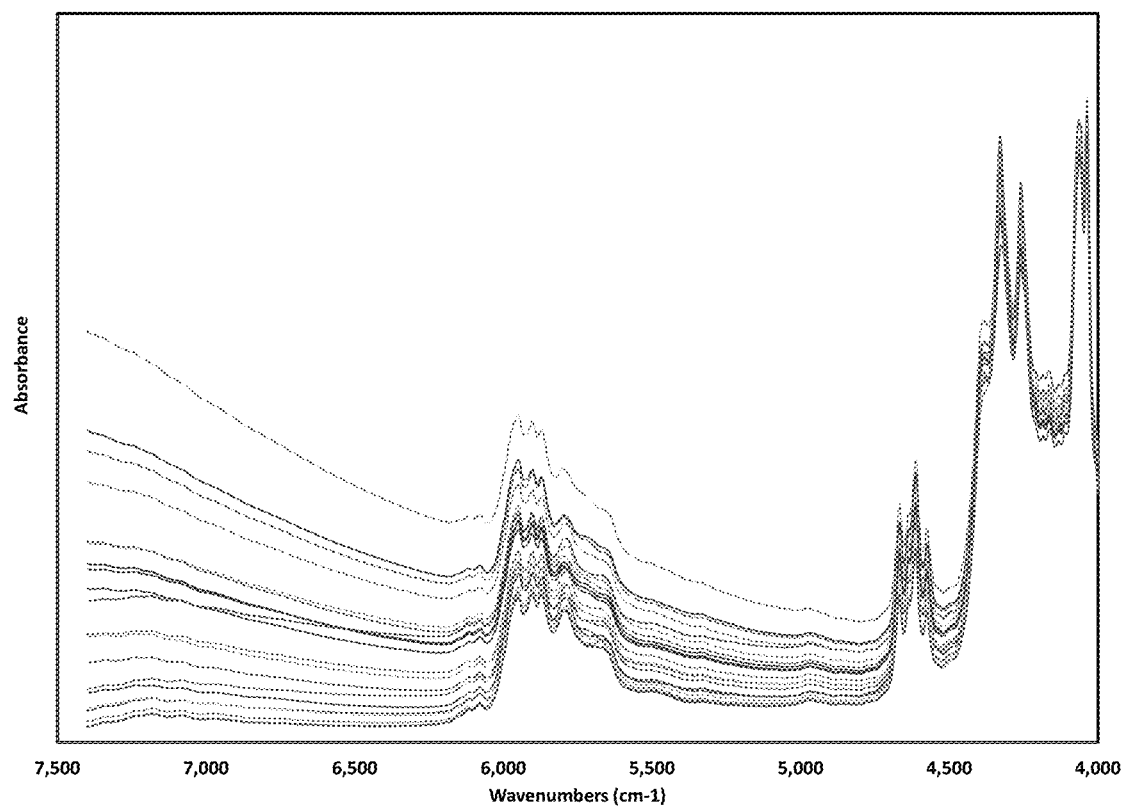
FIG. 1 displays overlaid examples of the NIR spectra for several example samples.

The following description of embodiments provides a non-limiting representative examples referencing numerals to particularly describe features and teachings of different aspects of the invention. The embodiments described should be recognized as capable of implementation separately, or in combination, with other embodiments from the description of the embodiments. A person of ordinary skill in the art reviewing the description of embodiments should be able to learn and understand the different described aspects of the invention. The description of embodiments should facilitate understanding of the invention to such an extent that other implementations, not specifically covered but within the knowledge of a person of skill in the art having read the description of embodiments, would be understood to be consistent with an application of the invention.

The present application generally pertains to methods and systems for predicting a blend compatibility of a blend of two, or three, or four or more oil compositions without actually blending the compositions together. Each of the two or more oil compositions in the contemplated blend may comprise asphaltene, maltenes, or both. Advantageously, the presently described methods and systems may be employed even when the individual components or the blend to be predicted comprises less than 1.5%, or even less than 1% by weight asphaltene. Advantageously, using the methods and systems herein the predicted blend compatibility is often consistent with a tested blend compatibility but avoids the need for testing the blend using, for example, titration methods or other techniques.

As used herein, asphaltenes may comprise primarily carbon, hydrogen, nitrogen, oxygen, and sulfur, as well as trace amounts of vanadium and nickel. The C:H ratio is approximately 1:1.2, depending on the asphaltene source. Asphaltenes are defined operationally as the n-heptane ($C_7H_{16}$)-insoluble, toluene ($C_6H_5CH_3$)-soluble component of a carbonaceous material such as crude oil, bitumen, or coal. Asphaltenes have been shown to have a distribution of molecular masses in the range of 400 u to 1500 u, but the average and maximum values are difficult to determine due to aggregation of the molecules in solution. Maltenes generally are n-alkane (pentane or heptane)-soluble molecular components and may comprise heavy, dark-colored asphaltic resins, first acidaffins, second acidaffins, and saturates, combined with lighter colored oils.

Predicting blend compatibility may be useful in regard to compositions from a crude oil, a refinery stream, a distillation cut, or a finished product. By accurately predicting blend compatibility one may determine the likelihood of fouling various types of equipment and take measures (automatically or otherwise) to prevent, hinder, or ameliorate such fouling due to potential incompatible blends.

Such measures may include, but are not limited to, making a change to the system if the prediction is incompatibility or precipitation of, for example, asphaltenes (if P<1 for the contemplated blend as explained below). Such changes are not particularly limited and may include a change in pressure, temperature, conversion, diversion of a stream, or any combination thereof to avoid producing the incompatible blend. Alternatively or additionally, the system may be configured to provide a signal to a user if P<1. Alternatively or additionally, the action taken based on the prediction of a potential incompatible blend may be to not implement the step, reaction, or other measure that contemplated the production of the incompatible blend.

The methods and systems may be used to predict blend compatibility irrespective of the number of components to be blended. For simplicity the methods and system will be described herein with reference to predicting blend compatibility in a system between a first oil composition A and a second oil composition B. However, it should be recognized that an ordinarily skilled artisan can readily extend the principles to blends with additional components. Also, while the principles are described herein relative to oil composition blends that may comprises asphaltenes and/or maltenes, the principles may be extended to blends of other components that are amenable to near infrared spectroscopy or even other analytical techniques.

The method generally comprises obtaining a correlation between near infrared spectroscopic information, asphaltene solubility parameter Ra, and maltene solubility parameter Po for a set of samples. In this regard both U.S. Pat. No. 11,236,281 and US2022/003976 are incorporated herein by reference. The correlation may be obtained in any convenient manner. For example, the correlation may be obtained by determining the asphaltene solubility parameter Ra and/or the maltene solubility parameter Po by titration on the set of samples and using multivariable analysis. One way of conducting the correlation is described in the examples below.

When the compatibility of a blend of a first oil composition A and a second oil composition B is to be predicted, a near infrared spectra analysis may be conducted to obtain near infrared spectra on composition A and composition B. The near infrared spectra and the above-described correlation may be used to obtain the Ra and Po for composition A and composition B. The Ra of the blend of the first oil composition A and the second oil composition B may be calculated using the equation Ra(blend)=mA RaA+mB RaB. The Po of the blend of the first oil composition A and the second oil composition B may be calculated using the equation Po(blend)=mA PoA+mB PoB. In the aforemented equations mA, mB are the % mass of crude oils A and B, while PoA, RaA, PoB and RaB are the parameters of the crude oils A and B that form the blend. Next, the blend compatibility may be predicted using the equation P=Po(blend)/Ra(blend) wherein a P≥1 indicates the blend is compatible.

If the blend contemplates a third oil composition C then the method may further comprise predicting the blend compatibility of a blend of the first oil composition A, the second oil composition B, and the third oil composition C using the principles above with the equations altered to contemplate the third component.

The methods described herein may be implemented into a refinery or refinery stream either inline or offline as desired. That is a near infrared spectrometer may be located on site or remote or even configured to be in line so that measurements may be taken in real time. In some embodiments a data processor may be configured to operate with the near infrared spectrometer and perform the aforementioned calculations to predict blend compatibility.

Examples

Materials and Sample Preparation

For the preparation of the calibration model, crude oils, and processed samples were evaluated using a well-established titration technique. For the NIR spectra recording, solutions of the samples were prepared in toluene containing 50 wt. % of sample.

Instrumentation

The NIR spectra (16 scans each) were recorded in transmission mode with a 0.5 mm pathlength $CaF_2$ cell using a Thermo 6700 FTIR spectrometer with a resolution of 4 $cm^{-1}$ in the range from 4,000 to 7400 $cm^{-1}$ (1.35-2.5 nm). All measurements were performed at room temperature. Thermo Scientific's TQ Analyst quantitative analysis software was used to develop a Partial Least Squares (PLS) regression algorithm.

FIG. 1 displays overlaid examples of the NIR spectra obtained for some of the toluene sample solutions. The NIR range between 4000 to 7500 $cm^{-1}$ was used for the analysis to focus on the first overtone localized at 7,400 to 4,500 $cm^{-1}$ for C—H stretches and the combination region localized at 5,200 to 4,000 $cm^{-1}$ for the C—H, C=H bonds. The spectra were smoothed, and the first derivative was calculated by using a first order polynomial function and window width of 3 and 5 points respectively.

Figure 2:
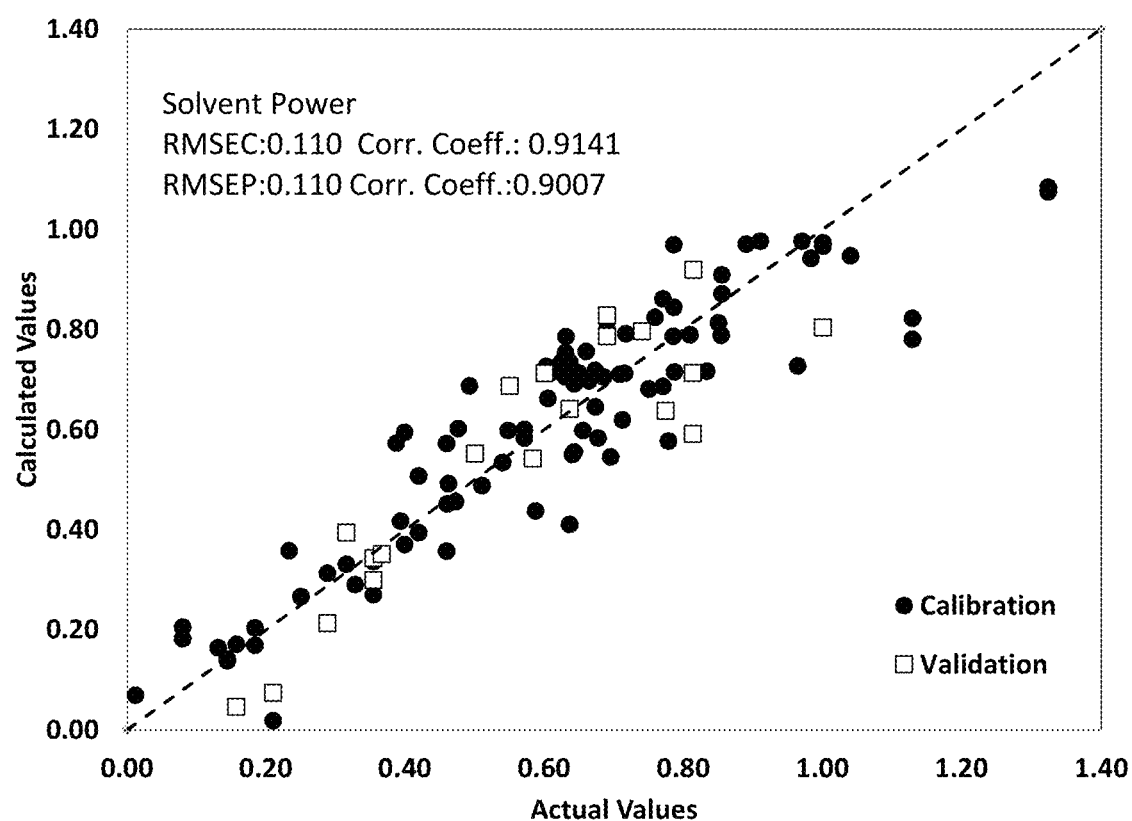
FIG. 2 represents a plot showing the correlation between calibration mixtures of Po crude component made by using the PLS regression methodology.

FIG. 2 represents a plot showing the correlation between calibration mixtures of Po crude component made by using the PLS regression methodology. The correlation is compared with the values obtain using titration measurements. 94 samples were used to develop calibration and 17 were used to validate the correlation.

The performance of the model is evaluated by determining the Root-Mean-Square Error of calibration (RMSEC) and the Root Mean Square Error of Prediction (RMSEP) on each single model predicted value for the samples. The values were ultimately established successively using PLS analysis. The RMSEC for the PLS regression model is 0.9141 and RMSEP is 0.9007 with five factors used. As inferred by the RMSEC and correlation coefficient, the PLS regression model performs well in the prediction of Po for the studied samples. The calibration model was validated by measuring 17 samples shown (FIG. 2: empty squares). These values were spread throughout the whole Po range.

Figure 3:
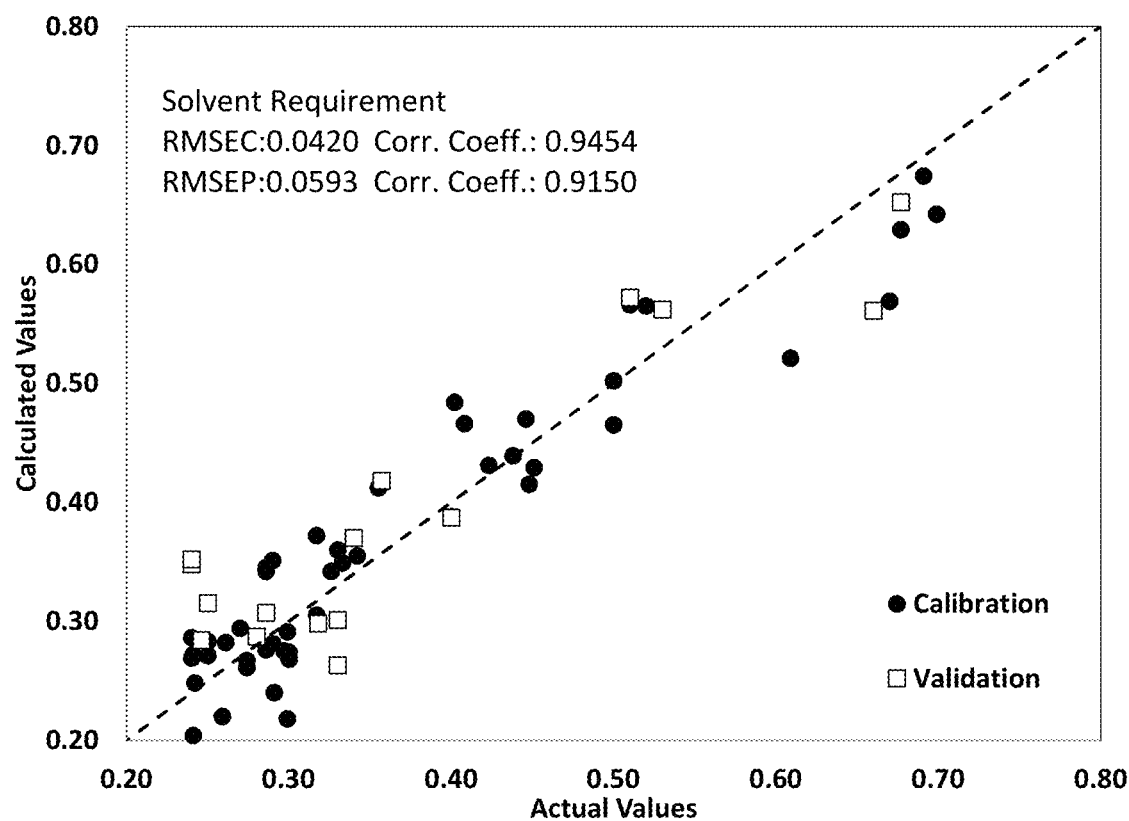
FIG. 3 shows the PLS regression correlation obtain for Ra.

FIG. 3 shows the PLS regression correlation obtain for Ra. In this plot, the correlation is compared with the values obtained using titration measurements. A group of 49 samples was used to develop the calibration and 16 samples (empty squares) were used to validate the correlation. The RMSEC for the PLS regression model is 0.9454 and RMSEP is 0.9150 with five factors. As inferred by the RMSEC and correlation coefficient, the PLS regression model performs well in the prediction of Ra.

The solubility parameter of the maltenes (also referred to as the solvent power of the maltenes) Po value and the solubility parameter of the asphaltenes (also called solvent requirement) Ra value of a blend can be calculated based on the values of the components determined using the Near IR models shown in FIG. 2 and FIG. 3. The calculation is based on the Regular Solution Theory described in Hildebrand, J. H. Solubility. xii. Regular solutions 1. J. Am. Chem. Soc. 1929, 51, 66-80 which article is incorporated herein by reference. According to this article which is the base for the titration techniques, Ra(blend) and Po(blend) are linear combinations of the parameters of the components following these blending rules:

$$Ra(blend) = mA\ RaA + mB\ RaB \quad (2)$$

$$Po(blend) = mA\ PoA + mB\ PoB \quad (3)$$

Where mA, mB are the % mass of crude oils A and B, while PoA, RaA, PoB and RaB are the parameters of the crude oils A and B that form the blend.

A series of blends were prepared using different crude oils. The Po and Ra values of the blends and their components were determining using the models shown in FIGS. 2 and 3 and the P-values were calculated according to equation (1) P=Po/Ra.

Figure 4:
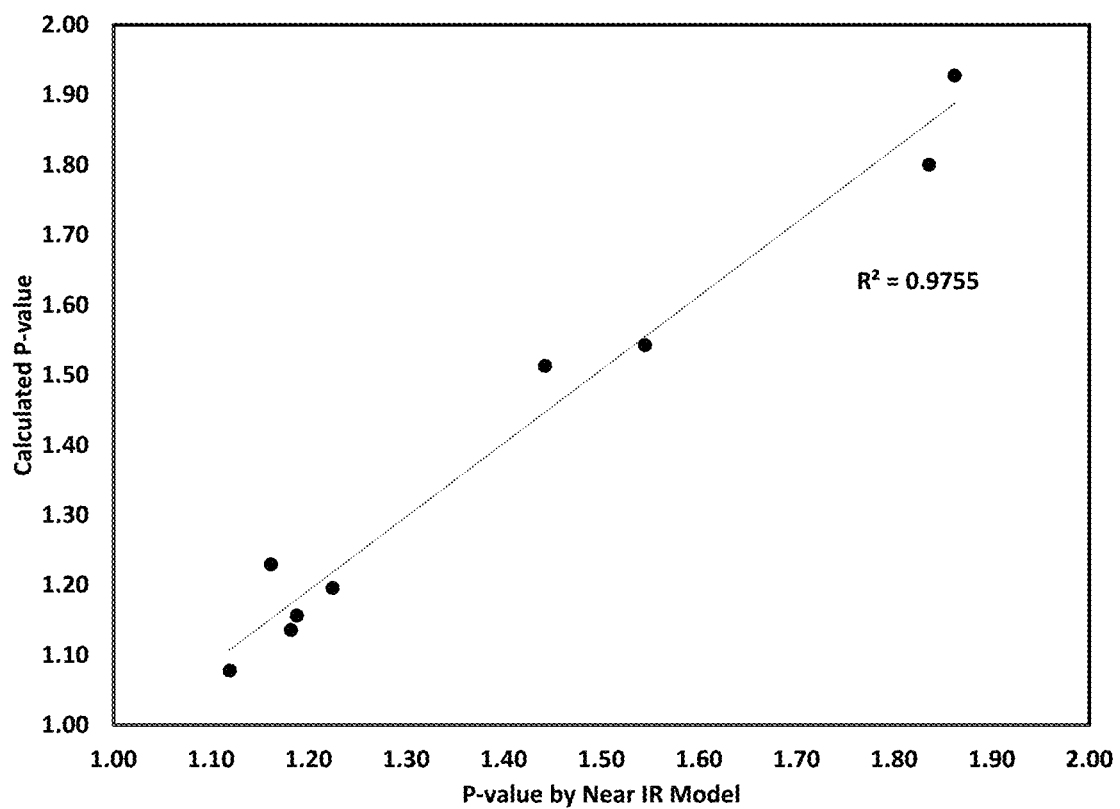
FIG. 4 shows a comparison between the P-values of blends determined using Near IR model described herein and the calculated values.

FIG. 4 shows a comparison between the P-values of blends determined using Near IR model as well as the values calculated using equations 2 and 3 together with equation 1 and Po and Ra values of the components from the Near IR model. The average difference between calculated P-values (blending rules) and experimental ones (from Near IR model) is 0.04. Differences between experimental and calculated values can vary from −0.07 to 0.07. Based on these results, a margin of error around ±0.07 on calculated P-values may be a reasonable consideration for practical applications. This margin of error is considerable lower than the value reported (±0.30) using the titration technique which is also supported by studies on nearly incompatible oils. See for example, Wiehe, I. A.; Kennedy, R. J. The oil compatibility model and crude oil incompatibility. Energy Fuels. 2000, 14, 56-59 and Rogel, E.; Hench, K.; Haj du, P.; Ingham, H. "The Role of Compatibility in Determining the Blending and Processing of Crude Oils" accept to be published in the ACS series Book "Application of Fundamental Chemistry in Addressing Upstream and DownstreamChallenges in the Petroleum Industry" 2019, both of which are incorporated herein by reference.

As shown above, the Near infrared spectroscopy techniques (NIR) developed and described herein offer an advantageous and accurate evaluation of both Po and Ra of hydrocarbon containing samples. The predictive ability of the Near IR regression model described herein is often superior to results obtained by titration. Additionally, the NIR methods are often much faster than the titration techniques, offer flexibility due to a portable instrument and may even be used for prediction of the parameters of blends when the specific blends are not available.

The above examples have been shown with reference to a blend of crude oils A and B. However, it should be appreciated that the principles described herein may be employed to predict compatibility of blends of more than two components, e.g., two, three, or even four or more components may be predicted. In addition, while the above examples relate to crude oils A and B, it should be appreciated that the principles may be applied to processed samples, diluents, or any other component wherein the above principles involving asphaltene solubility parameter Ra and maltene solubility parameter Po may be applicable.

In the preceding specification, various embodiments have been described with references to the accompanying drawings. It will, however, be evident that various modifications and changes may be made thereto, and additional embodiments may be implemented, without departing from the broader scope of the invention as set forth in the claims that follow. The specification and drawings are accordingly to be regarded as an illustrative rather than restrictive sense.

We claim:

1. A method of predicting a blend compatibility in a system between a first oil composition A and a second oil composition B, wherein the method comprises:
    obtaining a correlation between near infrared spectroscopic information, asphaltene solubility parameter Ra, and maltene solubility parameter Po for a set of samples using multivariable analysis;
    obtain a near infrared spectra on the first oil composition A and use the correlation to obtain the first oil composition A's Ra and Po;
    obtain a near infrared spectra on the second oil composition B and use the correlation to obtain the second oil composition B's Ra and Po;
    determine the Ra of the blend of the first oil composition A and the second oil composition B using the equation Ra(blend)=mA RaA+mB RaB and determine the Po of the blend of the first oil composition A and the second oil composition B using the equation Po(blend)=mA PoA+mB PoB, wherein mA, mB are the % mass of crude oils A and B, while PoA, RaA, PoB and RaB are the parameters of the crude oils A and B that form the blend;
    predict the blend compatibility using the equation P=Po(blend)/Ra(blend) wherein a P≥1 indicates the blend is compatible.

2. The method of claim 1 which further comprises making a change to the system if P<1.

3. The method of claim 2 wherein the change made to the system is a change in pressure, temperature, conversion, or any combination thereof.

4. The method of claim 1 which further comprises determining the asphaltene solubility parameter Ra by titration in the obtaining a correlation step.

5. The method of claim 1 which further comprises determining the maltene solubility parameter Po by titration in the obtaining a correlation step.

6. The method of claim 1 wherein the predicted blend compatibility is consistent with a tested blend compatibility.

7. The method of claim 1 wherein the first oil composition A comprises less than 1.5% by weight asphaltene.

8. The method of claim 1 wherein the first oil composition A comprises less than 1% by weight asphaltene.

9. The method of claim 1 wherein the second oil composition B comprises less than 1.5% by weight asphaltene.

10. The method of claim 1 wherein the second oil composition B comprises less than 1% by weight asphaltene.

11. The method of claim 1 wherein the system further comprises a third oil composition C and the method further comprises predicting the blend compatibility of a blend of the first oil composition A, the second oil composition B, and the third oil composition C.

12. A system for predicting a blend compatibility between a first oil composition A and a second oil composition B, wherein the system comprises:
a first oil composition A;
a second oil composition B;
a near infrared spectrometer configured to obtain a near infrared spectra on the first oil composition A and to obtain a near infrared spectra on the second oil composition B;
a data processor wherein the data processor is configured to:
use a correlation between near infrared spectroscopic information, asphaltene solubility parameter Ra, and maltene solubility parameter Po for a set of samples to obtain the first oil composition A's Ra and Po and the second oil composition B's Ra and Po;
determine the Ra of the blend of the first oil composition A and the second oil composition B using the equation Ra(blend)=mA RaA+mB RaB and determine the Po of the blend of the first oil composition A and the second oil composition B using the equation Po(blend) =mA PoA+mB PoB, wherein mA, mB are the % mass of crude oils A and B, while PoA, RaA, PoB and RaB are the parameters of the crude oils A and B that form the blend; and
predict the blend compatibility using the equation P=Po (blend)/Ra(blend) wherein a P≥1 indicates the blend is compatible.

13. The system of claim 12 wherein the system is configured to provide a signal to a user if P<1.

14. The system of claim 12 wherein the system is configured to take an automated action if P<1.

15. The system of claim 14 wherein the automated action is a change in pressure, temperature, conversion, or any combination thereof.

16. The system of claim 12 wherein the first oil composition A is a crude oil, a refinery stream, or a distillation cut, or a finished product.

17. The system of claim 12 wherein the second oil composition B is a crude oil, a refinery stream, a distillation cut, or a finished product.

18. The system of claim 12 which further comprises a third oil composition C and wherein the data processor is configured to predict the blend compatibility of a blend of the first oil composition A, the second oil composition B, and the third oil composition C.

19. The system of claim 12 wherein the first oil composition A, the second oil composition B, or both comprise less than 1% by weight asphaltene.

* * * * *